United States Patent
Gilkerson et al.

(10) Patent No.: US 7,580,746 B2
(45) Date of Patent: Aug. 25, 2009

(54) IMPLANTABLE MEDICAL DEVICE FOR GENERATING CARDIAC PRESSURE-VOLUME LOOP AND OPTIMIZING THERAPY

(75) Inventors: James O. Gilkerson, Stillwater, MN (US); Yongxing Zhang, Maple Grove, MN (US); Yunlong Zhang, Mounds View, MN (US); Sophia Wang, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 473 days.

(21) Appl. No.: 11/296,732

(22) Filed: Dec. 7, 2005

(65) Prior Publication Data

US 2007/0129765 A1  Jun. 7, 2007

(51) Int. Cl.
*A61N 1/365* (2006.01)

(52) U.S. Cl. .............................. 607/17; 607/18; 607/23; 607/24

(58) Field of Classification Search .................. 607/17, 607/18, 23, 24
See application file for complete search history.

(56) References Cited

U.S. PATENT DOCUMENTS

| | | | |
|---|---|---|---|
| 4,686,987 A | 8/1987 | Salo et al. | |
| 5,003,976 A | 4/1991 | Alt | |
| 5,154,171 A | 10/1992 | Chirife | |
| 5,190,035 A | 3/1993 | Salo et al. | |
| 5,368,040 A | 11/1994 | Carney | |
| 5,417,717 A | 5/1995 | Salo et al. | |
| 5,535,752 A | 7/1996 | Halperin et al. | |
| 5,564,434 A | 10/1996 | Halperin et al. | |
| 5,643,327 A | 7/1997 | Dawson et al. | |
| 5,792,195 A | 8/1998 | Carlson et al. | |
| 6,217,522 B1 * | 4/2001 | Shoshan | 600/490 |
| 6,278,894 B1 | 8/2001 | Salo et al. | |
| 6,409,675 B1 | 6/2002 | Turcott | |
| 6,438,408 B1 | 8/2002 | Mulligan et al. | |
| 6,522,914 B1 | 2/2003 | Huvelle et al. | |
| 6,567,700 B1 | 5/2003 | Turcott et al. | |
| 6,708,061 B2 | 3/2004 | Salo et al. | |
| 6,792,308 B2 | 9/2004 | Corbucci | |
| 7,212,861 B1 * | 5/2007 | Park et al. | 607/17 |
| 2003/0055461 A1 | 3/2003 | Girouard et al. | |
| 2004/0078060 A1 | 4/2004 | Ding et al. | |
| 2004/0122484 A1 | 6/2004 | Hatlestad et al. | |
| 2004/0172081 A1 | 9/2004 | Wang | |
| 2004/0186524 A1 | 9/2004 | Chinchoy | |
| 2004/0220637 A1 | 11/2004 | Zdeblick et al. | |
| 2004/0254483 A1 | 12/2004 | Zdeblick et al. | |

(Continued)

FOREIGN PATENT DOCUMENTS

EP 1169085 8/2004

*Primary Examiner*—Carl H Layno
*Assistant Examiner*—Yun Haeng Lee
(74) *Attorney, Agent, or Firm*—Faegre & Benson LLP

(57) ABSTRACT

An implantable medical device for generating a cardiac pressure-volume loop, the implantable medical device comprising a pulse generator including control circuitry, a first cardiac lead including a proximal end and a distal end and coupled to the pulse generator at the proximal end, a first electrode located at the distal end of the cardiac lead and operatively coupled to the control circuitry, a sound sensor operatively coupled to the control circuitry, and a pressure sensor operatively coupled to the control circuitry, wherein the implantable medical device is adapted for measuring intracardiac impedance. A method of using the implantable medical device to optimize therapy delivered to the heart.

10 Claims, 10 Drawing Sheets

U.S. PATENT DOCUMENTS

2005/0102001 A1 5/2005 Maile et al.
2005/0137490 A1 6/2005 Scheiner et al.
2005/0182330 A1 8/2005 Brockway et al.
2006/0041281 A1 2/2006 Von Arx et al.

* cited by examiner

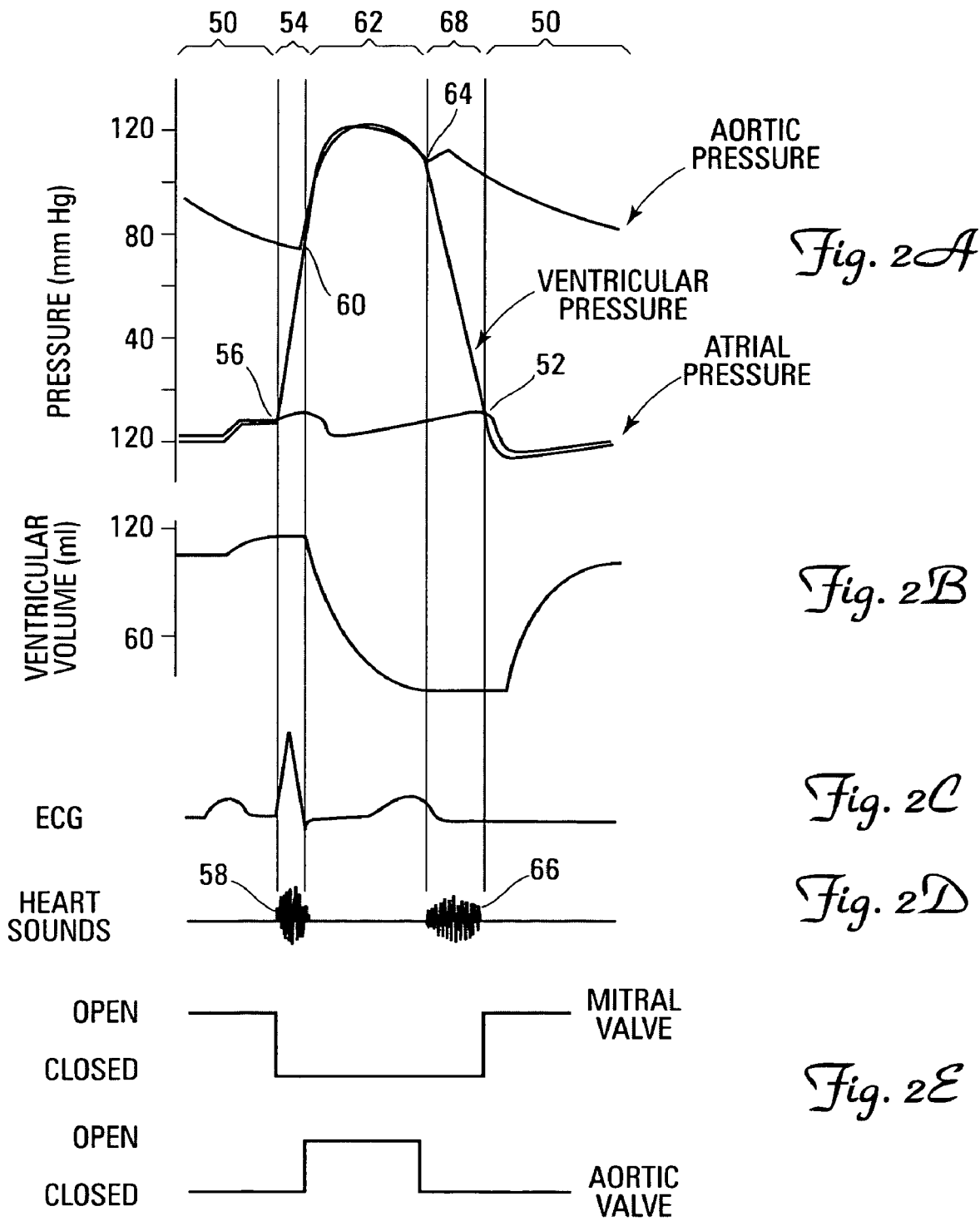

IMPLANTABLE MEDICAL DEVICE FOR GENERATING CARDIAC PRESSURE-VOLUME LOOP AND OPTIMIZING THERAPY

TECHNICAL FIELD

The present invention relates to devices and methods for determining the pressure-volume loop of a heart. More particularly, the present invention relates to monitoring the heart and optimizing therapy based on the pressure-volume loop.

BACKGROUND

Implantable medical devices such as implantable pacemakers and defibrillators monitor the heart's rhythm by sensing electrical signals. If a device detects an abnormal heart rhythm, or arrhythmia, it delivers therapy in the form of an electrical pulse. While such devices detect arrhythmias and take action to restore the heart's normal sinus rhythm, they can neither detect nor take corrective actions for other forms of cardiac malfunctions stemming from pathological conditions of the heart such as abnormal cardiac volume, abnormal cardiac pressure, and malfunctioning cardiac valves.

Stethoscopes have been used for many years to diagnose pathological conditions of the heart based on cardiac sounds. Examples of such cardiac sounds include the S1 and S2 heart sounds, which respectively comprise the "lub" and the "dub" of the "lub-dub" rhythm of the heart. The S1 heart sound is generated when the mitral and tricuspid valves close. The S2 heart sound is generated when the pulmonary and aortic valves close. Conditions identifiable based upon cardiac sounds comprise aortic insufficiency, atrial septal defect, coarctation of the aorta, early systolic murmur, Ebstein's Anomaly, ejection click, late systolic murmur, mitral stenosis, mitral valve prolapse, opening snap, pansystolic murmur, pulmonary stenosis, S1 splitting, S2 splitting, venous hum, ventricular septal defect, arrhythmia, valve operation, patent ductus ateriosus, etc.

The performance of the heart can also be evaluated by measuring cardiac parameters. Such cardiac parameters include cardiac volume, cardiac stroke, stroke volume, stroke flow rate, cardiac ejection fraction, cardiac pressure, and blood pressure within a blood vessel in the immediate vicinity of the heart.

There remains a need for an improved implantable medical device capable of evaluating the performance of the heart based on the relationship between the heart's electrical signals, sounds, and cardiac parameters. There also remains a need for an improved implantable medical device capable of optimizing therapy delivered to the heart based on the relationship between the heart's electrical signals, sounds, and cardiac parameters, and a method of optimizing therapy delivered to the heart based on that relationship.

SUMMARY

The present invention, according to one embodiment, is an implantable medical device for generating a cardiac pressure-volume loop, the implantable medical device comprising a pulse generator including control circuitry, a first cardiac lead including a proximal end and a distal end and coupled to the pulse generator at the proximal end, a first electrode located at the distal end of the cardiac lead and operatively coupled to the control circuitry, a sound sensor operatively coupled to the control circuitry, and a pressure sensor operatively coupled to the control circuitry, wherein the implantable medical device is adapted for measuring intracardiac impedance. According to another embodiment, the implantable medical device further comprises a first coil coupled to the first cardiac lead and operatively coupled to the control circuitry, wherein the intracardiac impedance is measured between the first coil and the first electrode.

The present invention, according to another embodiment, comprises a method of generating a pressure-volume loop for a heart using an implantable medical device including a pulse generator, control circuitry, a cardiac lead having a proximal end and a distal end, an electrode coupled to the distal end of the cardiac lead, a sound sensor, a pressure sensor, and adapted for measuring cardiac volume. The method comprises creating a first corner of the pressure-volume loop by recording a first cardiac pressure and first cardiac volume at a first time associated with an S1 heart sound, creating a second corner of the pressure-volume loop by monitoring the cardiac pressure and volume until a second time at which the cardiac volume starts decreasing, and recording a second cardiac pressure and second cardiac volume at that time, creating a third corner of the pressure-volume loop by recording a third cardiac pressure and third cardiac volume at a third time associated with an S2 heart sound and creating a fourth corner of the pressure-volume loop by monitoring the cardiac pressure and volume until a fourth time at which the cardiac volume increases rapidly, and recording a fourth cardiac pressure and fourth cardiac volume at that time. According to yet another embodiment, the cardiac volume is calculated based on the intracardiac impedance measured by the implantable medical device.

Another embodiment of the invention comprises a method for modifying therapy delivered to a heart using an implantable medical device including a pulse generator, control circuitry, a cardiac lead having a proximal end and a distal end, an electrode coupled to the distal end of the cardiac lead, a sound sensor, a pressure sensor, and adapted for measuring cardiac volume. The method comprises generating a baseline pressure-volume loop using the implantable medical device, storing the baseline pressure-volume loop in the control circuitry, generating a pressure-volume loop at a specified interval, comparing the generated pressure-volume loop to the baseline pressure-volume loop, determining if there is a significant change in a cardiac parameter based on the comparison, and modifying the therapy delivered to the heart in response to the significant change.

The present invention, according to yet another embodiment, comprises a method for modifying therapy delivered to a heart using an implantable medical device including a pulse generator, control circuitry, a cardiac lead having a proximal end and a distal end, an electrode coupled to the distal end of the cardiac lead, a sound sensor, a pressure sensor, and adapted for measuring cardiac volume. The method comprises detecting an increase in a heart rate using the electrode, generating a first pressure-volume loop, determining if fibrillation is occurring based on the first pressure-volume loop, and delivering defibrillation therapy.

BRIEF DESCRIPTION OF THE DRAWINGS

FIGS. 2A-2E illustrates various parameters indicative of cardiac operation and performance.

DETAILED DESCRIPTION

Figure 1:
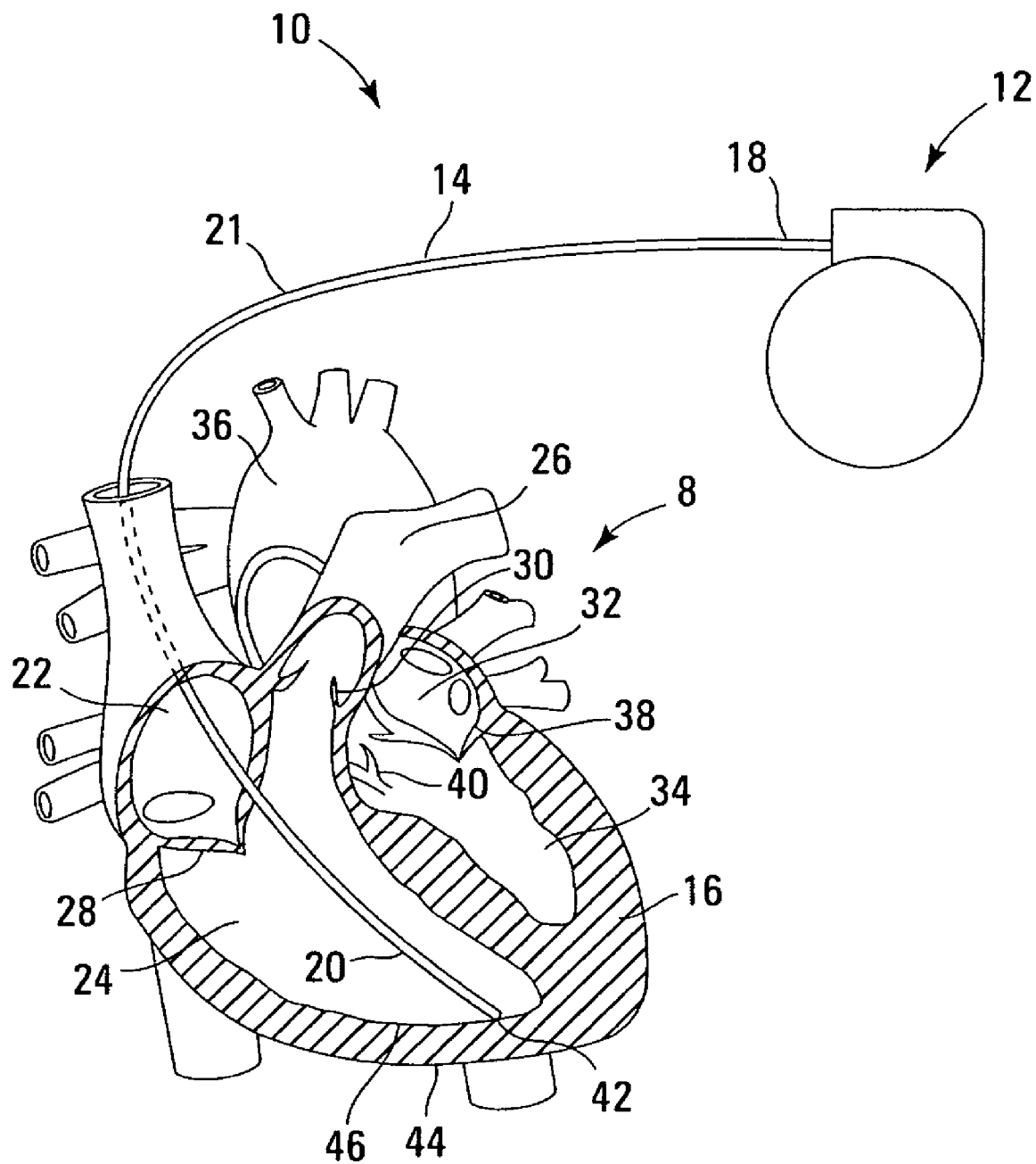
FIG. 1 is a combined cutaway view of a heart and a perspective view of an implantable medical device according to one embodiment of the present invention.

FIG. 1 is a combined cutaway view of a human heart 8 and a perspective view of an implantable medical device (IMD) 10. The IMD 10 includes a pulse generator 12 and a cardiac lead 14. The cardiac lead 14 operates to convey electrical signals between the heart 8 and the pulse generator 12. The proximal end 18 of the cardiac lead 14 is coupled to the pulse generator 12, and the distal end 20 of the cardiac lead 14 is coupled to the heart 8. The cardiac lead 14 includes a lead body 21 extending from the proximal end 18 to the distal end 20. The cardiac lead 14 can comprise a brady lead, a tachy lead, a heart failure lead, a pulmonary artery lead, a left side lead implantable in the left atrium and/or the left ventricle, a right side lead implantable in the right atrium and/or the right ventricle, or any other lead as is known in the art.

The heart 8 comprises a myocardium or cardiac muscle 16, a right atrium 22, a right ventricle 24, and a pulmonary artery 26. A tricuspid or atrioventricular valve 28, located between the right atrium 22 and the right ventricle 24, controls blood flow from the right atrium 22 to the right ventricle 24. A pulmonary valve 30, located between the right ventricle 24 and the pulmonary artery 26, controls blood flow from the right ventricle 24 to the pulmonary artery 26. The heart 8 further comprises a left atrium 32, a left ventricle 34, and an aorta 36. A mitral or atrioventricular valve 38, located between the left atrium 32 and the left ventricle 34, controls blood flow from the left atrium 32 to the left ventricle 34. An aortic valve 40, located between the left ventricle 34 and the aorta 36, controls blood flow from the left ventricle 34 to the aorta 36.

In the embodiment shown in FIG. 1, the distal end 20 of the cardiac lead 14 is implanted in the right ventricle 24 and the electrode 42 is attached to the endocardium or inner layer 46 of the heart 8. The electrode 42 may both sense electrical signals of the heart 8 and deliver electrical pulses to the heart 8 in an attempt to correct an arrhythmia and restore sinus rhythm. In other embodiments, the cardiac lead 14 may be implanted or placed within any chamber of the heart 8, as is well known in the art. For example, the distal end 20 of the cardiac lead 14 may be implanted in the right atrium 22 or the left ventricle 34. In another embodiment, the lead is an epicardial lead and the electrode is attached to the epicardium 44. In alternative embodiments, the electrode 42 may be implanted through the epicardium 44 or endocardium 46 and into the myocardium 16. In another embodiment of the present invention, the IMD 10 may include a plurality of cardiac leads 14, each with their distal end 20 placed in, implanted in, or attached to a different chamber, or a different part of the heart 8.

FIGS. 2A-2E depict various parameters of the left side of a normal heart 8 during a cardiac cycle. FIG. 2A depicts the aortic pressure, ventricular pressure, and atrial pressure of the heart 8. FIG. 2B depicts the ventricular volume of the heart 8 during a cardiac cycle. FIG. 2C depicts an electrocardiogram (ECG or egram) for the heart 8. FIG. 2D depicts heart sounds made by the heart 8. FIG. 2E depicts the status (open or closed) of the mitral valve 38 and the aortic valve 40 during a cardiac cycle.

The cardiac cycle begins with ventricular filling 50 when the mitral valve 38 opens at 52 because the ventricular pressure falls below atrial pressure (FIG. 2A). During ventricular filling 50, the aortic pressure slowly decreases (FIG. 2A). The isovolumetric stage 54 of ventricular contraction begins and the mitral valve 38 closes at 56, generating the S1 heart sound 58 (FIG. 2D) when ventricular pressure exceeds atrial pressure (FIG. 2A). The isovolumetric contraction phase 54 continues until the ventricular pressure equals the aortic pressure at 60 (FIG. 2A). At this point 60, the aortic valve 40 opens and the ejection phase 62 begins (FIG. 2A). The ejection phase 62 continues until the ventricular pressure falls below the aortic pressure at 64, at which point the aortic valve 40 closes (FIG. 2A), generating the S2 heart sound 66 (FIG. 2D). The isovolumetric relaxation phase 68 begins and ventricular pressure falls rapidly until it is exceeded by atrial pressure, at which point the mitral valve 38 opens and the cycle repeats (FIG. 2A).

Cardiac pressure curves for the pulmonary artery 26, the right atrium 22, and the right ventricle 24, and the cardiac volume curve for the right ventricle 24, similar to those illustrated in FIGS. 2A-2B for the left part of the heart 8, may be generated. Typically, the cardiac pressure in the right ventricle 24 is lower than the cardiac pressure in the left ventricle 34.

Figure 3A:
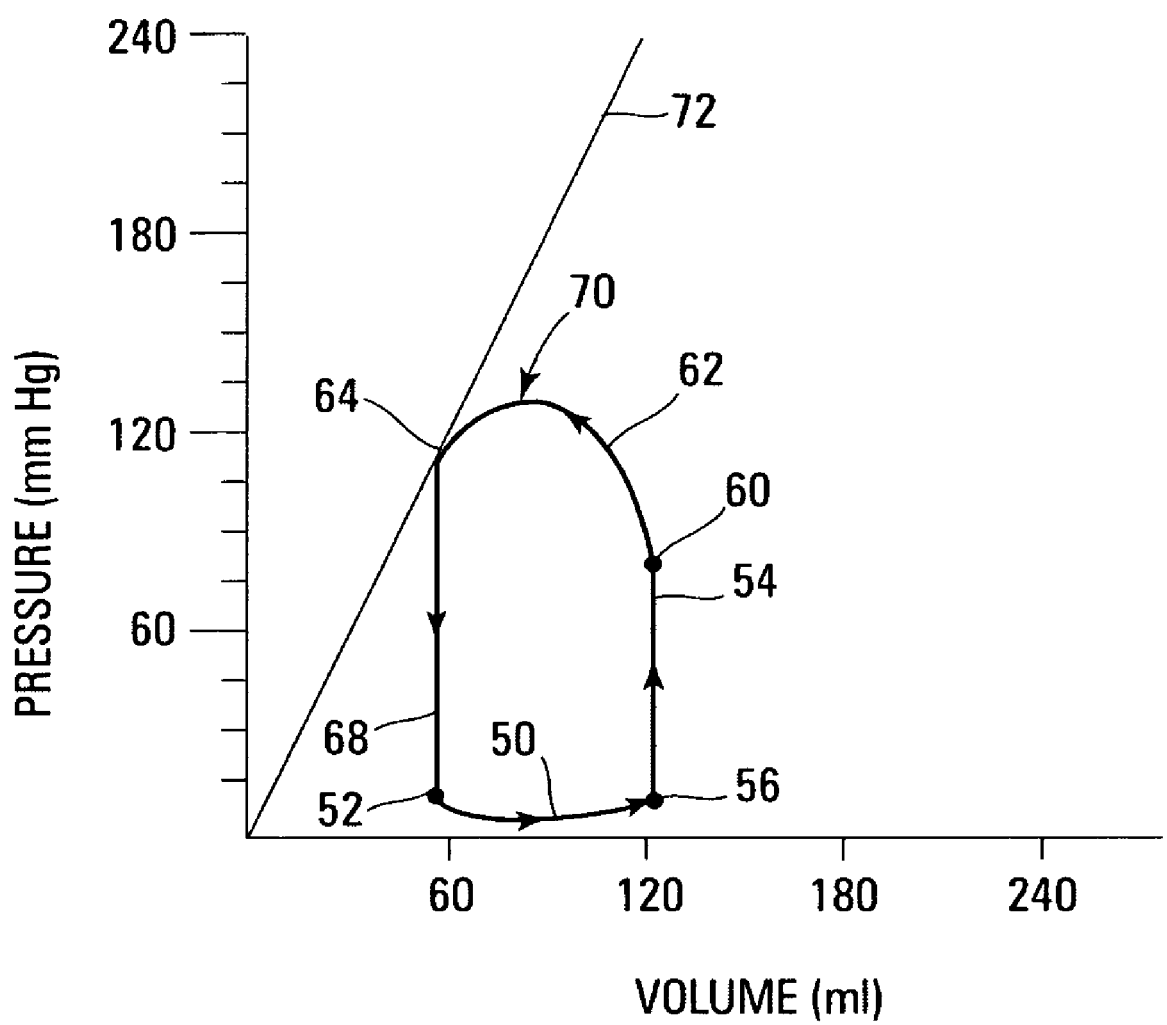
FIGS. 3A-3F depict various pressure-volume loops for the left ventricle of a human heart.

FIG. 3A illustrates another method of representing pressure and volume parameters of the heart 8 known as a pressure-volume (PV) loop. PV loops can be used to measure the performance of the heart 8. A loop 70 shows normal PV characteristics for the left ventricle 34 of the heart 8. The loop 70 moves in a counter-clockwise direction. The mitral valve 38 opens and ventricular filling 50 begins at the point 52 on the loop 70. The ventricular filling 50 ends at the point 56 with closure of the mitral valve 38. The point 56 represents the end diastolic volume (EDV) or the volume of blood in the heart 8 at the end of its dilatation phase. As described above, the S1 heart sound 58 occurs at the point 56. The isovolumetric contraction phase 54 begins at the point 56 and continues until the aortic valve 40 opens at the point 60. The ejection phase 62 lasts from the aortic valve 40 opening at the point 60 until the aortic valve 40 closes at the point 64. The closure of the aortic valve 40 at the point 64 generates the S2 heart sound 66 and also marks the end systolic volume (ESV), or the volume of blood in the heart 8 at the end of its contraction phase. The isovolumetric relaxation phase 68 begins at the point 64 and continues until the mitral valve 38 opens at the point 52 and the cycle repeats. The PV loop 70 can be approximated if the points 52, 56, 60, and 64 (the four "corners" of the PV loop) are known.

The contractility index, or the capacity of the muscle for becoming shorter in response to a suitable stimulus, of the heart 8 can be estimated by calculating the slope of the end systolic pressure-volume line (shown as 72). The stroke work is the area of the PV loop 70. The stroke volume is equal to the EDV minus the ESV and is the amount of blood ejected from the heart with each heart beat. The ejection fraction (the proportion of the volume of blood in the ventricles at the end of diastole that is ejected during systole) it is the stroke volume divided by the EDV.

Figure 3B:
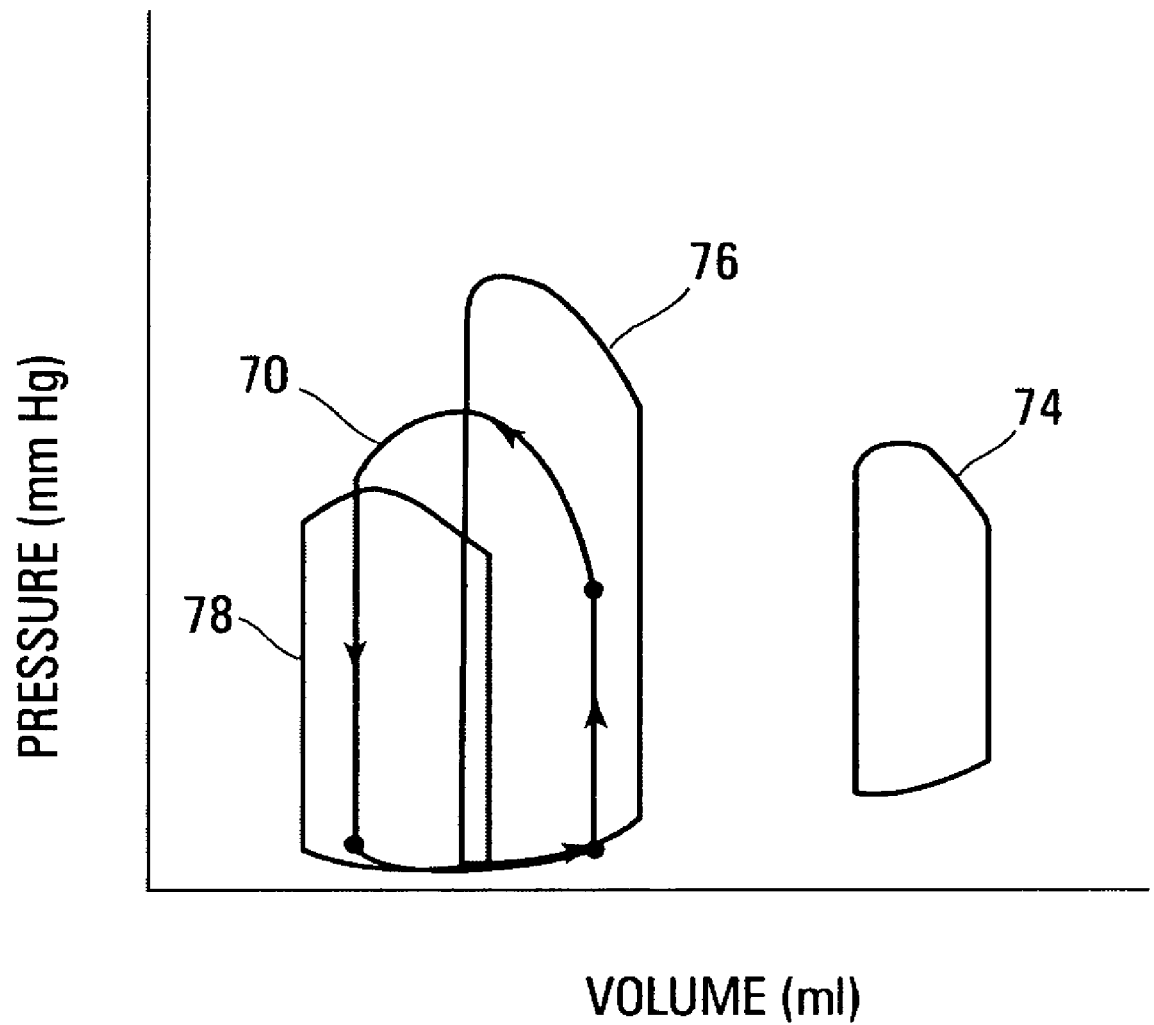

FIG. 3B illustrates how a variety of abnormalities in the heart 8 result in changes in the PV loop. PV loop 74 is representative of congestive heart failure. The PV loop 74 is shifted to the right of the normal PV loop 70. The PV loop 74 also has a substantially smaller stroke volume than the stroke volume of the normal PV loop 70 and lower peak pressure than the PV loop 70. The PV loop 76 is representative of aortic stenosis. The stroke volume is reduced and the ESV is increased compared to the normal PV loop 70. Mitral stenosis is represented by PV loop 78. In this case, the ESV increases slightly while the EDV is decreased, as is the stroke volume. Additional abnormal cardiac conditions can be identified using the PV loop as is known in the art.

Figure 3C:
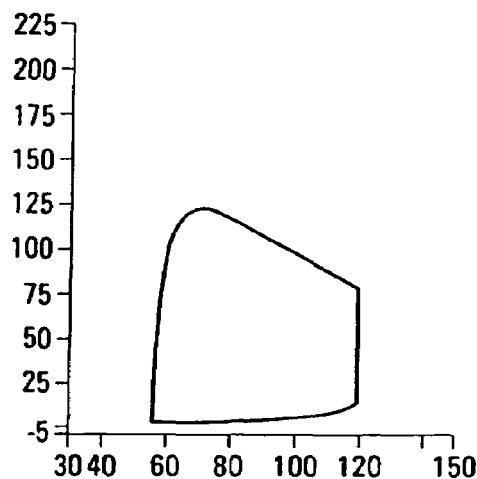
Figure 3D:
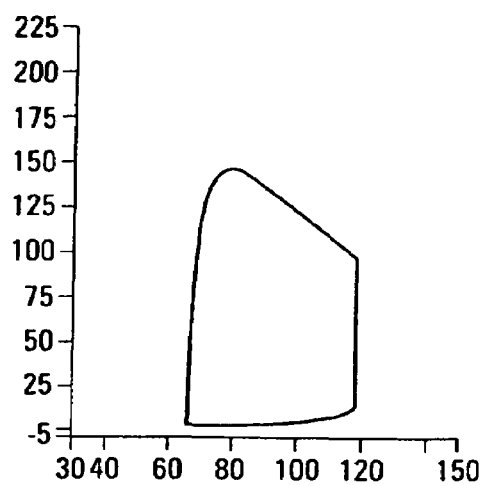
Figure 3E:
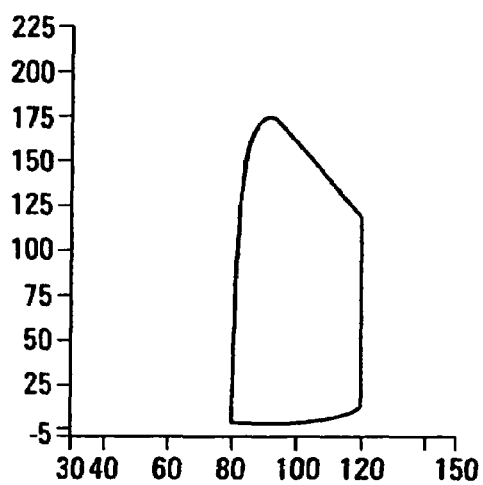
Figure 3F:
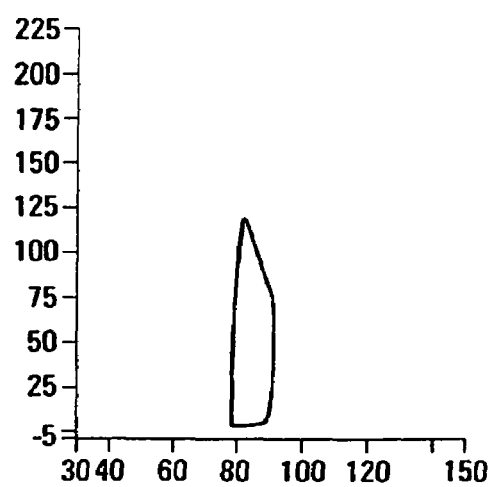

FIGS. 3C-3F illustrate the changes that occur in the PV loop as the heart rate increases. FIG. 3C depicts a PV loop at a heart rate of 72 beats per minute ("bpm"). FIGS. 3D and 3E depict PV loops at heart rates of 102 bpm and 150 bpm, respectively. FIG. 3F depicts a PV loop at a heart rate of 180 bpm. As shown in FIG. 3F, the PV loop is narrowing, indicating a decrease in the stroke volume and corresponding decrease in the volume of blood ejected from the heart. As the heart rate increases beyond 180 bpm during fibrillation, the PV loop will continue to shrink until it resembles a dot or small square.

Figure 4:
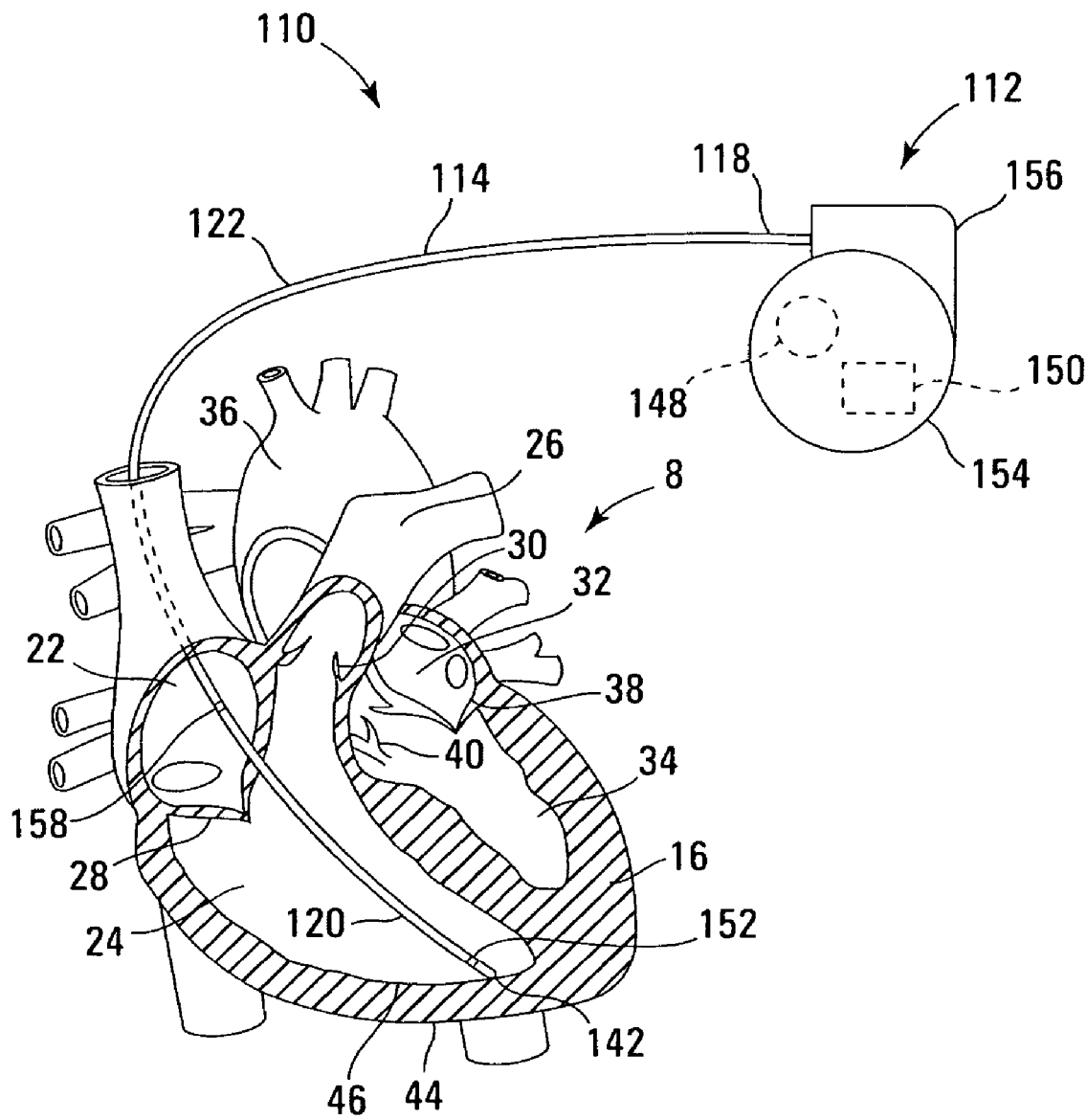
FIG. 4 is a perspective view of an implantable medical device according to one embodiment of the present invention.

FIG. 4 is a perspective view of an IMD 110 adapted for generating a PV loop. The IMD 110 comprises a pulse generator 112, a cardiac lead 114, and an electrode 142. The pulse generator 112 includes a housing 154 and a header 156. A sound sensor 148 for detecting cardiac sounds and control circuitry 150 are located within the housing 154. The sound sensor 148 can comprise a hydrophone, a nano-stethoscope, an acoustic sensor, an accelerometer, a microphone, an acoustic Micro Electro-Mechanical System (MEMS), or any other sensor suitable for sensing heart sounds. In alternative embodiments, the sensor 148 could be located in the header 156 or at the distal end 120 of the cardiac lead 114 for placement in the heart 8. The sensor 148 could also be located within a blood vessel or in the vicinity of a cardiac valve. One such device and method for monitoring cardiac sounds using an accelerometer is disclosed in U.S. Pat. No. 5,792,195 to Carlson et al., which is hereby incorporated by reference in its entirety. Use of an accelerometer for detecting heart sounds is also described in U.S. Publication No. 2005/0137490 and U.S. Publication No. 2005/0102001, both of which are hereby incorporated by reference in their entirety. Another device and method for monitoring broadband sounds using an acoustic sensor is disclosed in commonly assigned U.S. patent application No. 11/212,176, hereby incorporated by reference in its entirety. In one embodiment, the sensor 148 is connected to the circuitry 150 via a conductive member (not shown) extending through the cardiac lead 114. In another embodiment, the sensor 148 is coupled to the circuitry using any wireless communication technique known in the art.

As shown in FIG. 4, a pressure sensor 152 is coupled to the distal end 120 of the cardiac lead 114. The pressure sensor 152 may be placed within or in the vicinity of the heart 8 or within a blood vessel. For example, the pressure sensor 152 may be implanted in the right ventricle 24, the pulmonary artery 26, the left atrium 32, or the left ventricle 34. In one embodiment, the pressure sensor 152 is not coupled to the lead 114 but instead is remote from the lead 114. In one embodiment, the remote pressure sensor 152 is connected to the circuitry 150 via a conductive member (not shown). In another embodiment, the pressure sensor 152 is coupled to the circuitry 150 using any wireless communication technique known in the art. The pressure sensor 152 can comprise a MEMS device, a piezoelectric sensor, a capacitor-Micromachined Ultrasonic Transducer (cMUT), a condenser, a micro-monometer, or any other sensor adapted for measuring cardiac pressure. Alternate devices and methods for measuring cardiac pressure are disclosed in U.S. Pat. No. 5,368,040 to Anderson, U.S. Pat. No. 5,535,752 to Halperin et al., U.S. Pat. No. 5,564,434 to Halperin et al., and U.S. Patent Application Publication No. 2005/0182330 to Brockway et al., all of which are herein incorporated by reference in their entirety.

A coil 158 is coupled to the cardiac lead 114, and in the embodiment shown in FIG. 4, is located in the right atrium 22. The control circuitry 150 can derive cardiac volume from intracardiac impedance measurements made between the electrode 142 and the coil 158. The volume of blood, V, equals the resistivity of blood multiplied by the square of the distance between the intracardiac impedance measurement devices and divided by the intracardiac impedance. By connecting a high frequency oscillator (not shown) having a constant current characteristic between the coil 158 and the electrode 148, a signal can be derived proportional to the instantaneous intracardiac impedance developed between the coil 158 and the electrode 142. This intracardiac impedance measurement is then used to calculate volume.

In alternative embodiments, the intracardiac impedance measurement can be taken between two coils 158, between two electrodes 142, or using any other method as is known in the art. The left ventricular intracardiac impedance is most accurately measured using a left ventricular lead configuration. In one embodiment, the left ventricular intracardiac impedance is measured between an electrode 142 at the distal end of a left ventricular lead and an electrode 142 at the distal end of a right atrial lead. The right ventricular intracardiac impedance can be measured using a right ventricular lead configuration. In one embodiment, the intracardiac impedance is measured between an electrode 142 at the distal end of a right ventricle lead and a distal coil 158. The distal coil 158 can be located in the right atrium 22, as is shown in FIG. 4. In another embodiment, the intracardiac impedance is measured between an electrode 142 at the distal end of a right ventricle lead and an electrode 142 at the distal end of a right atrial lead. In alternative embodiments, the IMD 110 can include a plurality of cardiac leads 114 and the intracardiac impedance can be measured between the electrodes 142 and/or coils 158 on the leads 114. The leads may be endocardial, epicardial, or myocardial leads, or any combination thereof.

Various devices and methods for measuring intracardiac impedance and/or calculating cardiac volume based on intracardiac impedance are described in U.S. Pat. No. 5,003,976 to Alt, U.S. Pat. No. 6,278,894 to Salo et al., U.S. Pat. No. 4,686,987 to Salo et al., U.S. Pat. No. 5,190,035 to Salo et al., U.S. Pat. No. 5,417,717 to Salo et al., and U.S. Pat. No. 5,154,171 to Chirife, and in commonly assigned U.S. patent application Ser. No. 11/208,922, filed Aug. 22, 2005, all of which are herein incorporated by reference in their entirety.

Figure 5:
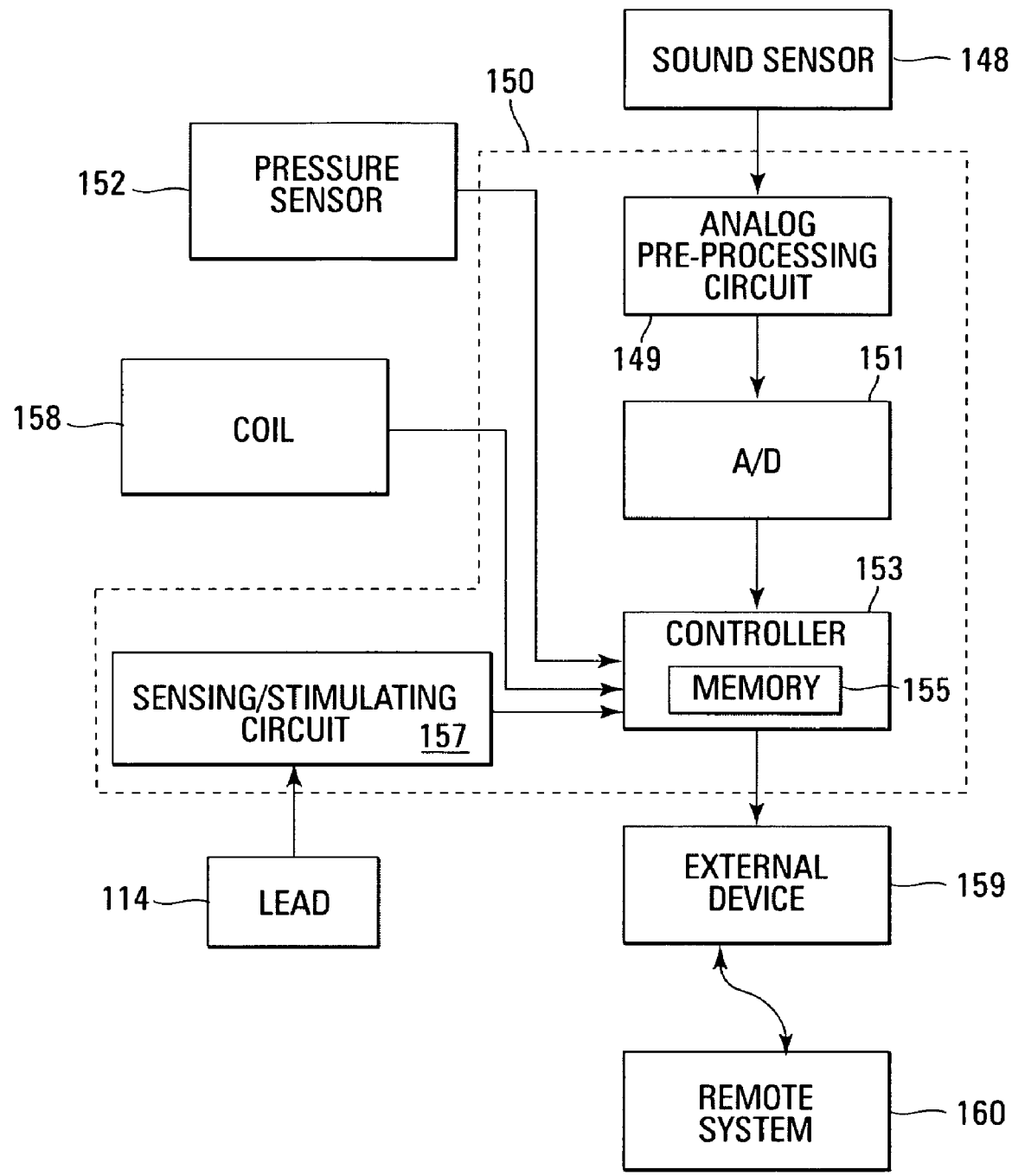
FIG. 5 depicts the control circuitry and system of the implantable medical device of FIG. 4.

FIG. 5 shows at least a portion of the circuitry 150 for processing the signals received from the sensor 148, the pressure sensor 152, the coil 158, and the electrode 142. The signal from the sound sensor 148 is processed by an analog preprocessing circuit 149, which may include a filter and/or an amplifier. The signal is then directed to an analog-to-digital converter 151. The digital signal is then directed to a microprocessor or controller 153 for analysis, and may be stored in memory 155. The controller 153 also receives signals from the pressure sensor 152 and the coil 158. The circuitry 150 may also include a sensing/stimulating circuit 157 for processing the electrical signals received from or delivered to the lead 114. In one embodiment, the sensing/stimulating circuit 157 generates an egram, which is provided to the controller 153. In another embodiment, the controller 153 uses the signal received by the sensing/stimulating circuit in conjunction with the signal from the coil 158 to generate the cardiac volume. The control circuitry 150 can collect cardiac data including one or more cardiac pressures, one or more intracardiac impedances, and one or more cardiac sounds during one or more cardiac cycles. The control circuitry 150 can store and manipulate the collected cardiac data to evaluate the performance of the heart 8.

In one embodiment, the system further includes an external device 159, which is operatively coupled to the circuitry 150 by, for example, a wireless RF communication link. The external device 159 may, for example, be an external programmer adapted for use with the implanted medical device 110. This external device 159 is, in turn, coupled to a remote system 160. The external device 159 and remote system 160 may, for example, be coupled by a telephone line, electrical or optical cable, RF interface, satellite link, local area network or wide area network. The remote system 160 allows a user (e.g., a physician or clinician) located at a remote location to obtain data relating to the heart sounds and to conduct or aid in the diagnosis of a patient based on such data. In one embodiment, the remote system 160 includes an advanced patient management system, such as is disclosed in U.S. Publication 2004/0122484, which is hereby incorporated by reference in its entirety.

Figure 6:
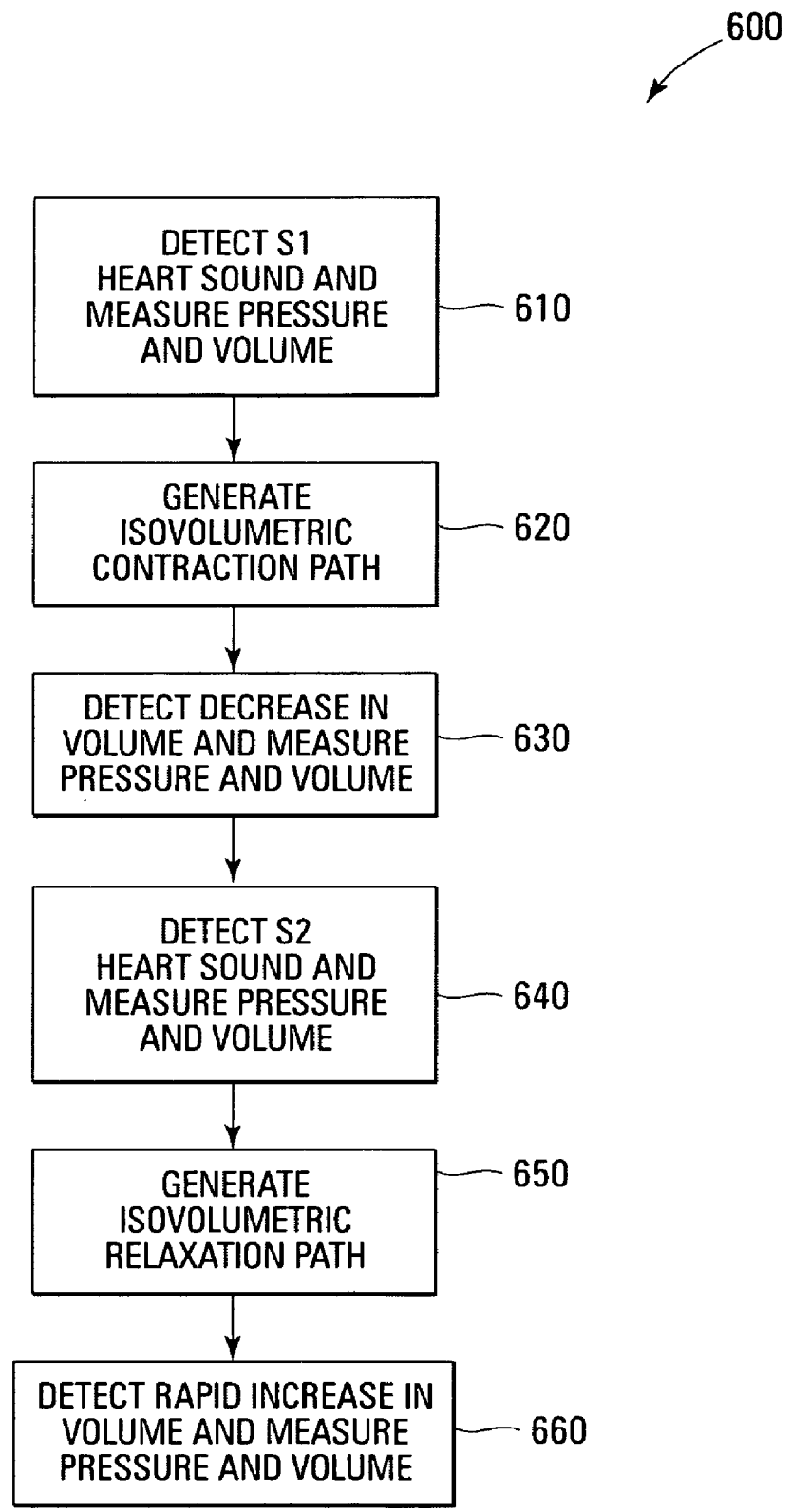
FIG. 6 illustrates an exemplary method of using the implantable medical device of FIG. 4 to generate a pressure-volume loop.

FIG. 6 shows an exemplary method 600 of generating a PV loop for the heart 8 using circuitry 150. As described above, the S1 heart sound 58 corresponds to closure of the mitral valve 38 at the point 56. The sound sensor 148 can be used to detect the S1 heart sound 58 (block 610). At the point 56, the cardiac pressure measurements can be taken by the pressure sensor 152 and intracardiac impedance measurements taken between the electrode 142 and the coil 158 can be used to calculate the volume, thus resulting in generation of one of the four "corners" of the PV loop 70.

Intracardiac impedance measurements between the electrode 142 and the coil 158 and pressure measurements taken by the pressure sensor 152 can be used by the control circuitry 150 to generate the path of isovolumetric contraction 54 (block 620). The opening of the aortic valve 40 at point 60 (the second "corner" of the PV loop 70) can be determined by the control circuitry 150 as the instant that the cardiac volume starts decreasing while the cardiac pressure continues to increase (block 630). The closure of the aortic valve 40 at the point 64 generates the S2 heart sound 66, which can be detected by the sensor 148 (block 640). The pressure measurement taken by the pressure sensor 152 and the volume measurement calculated by the control circuitry 150 based on the intracardiac impedance measurements between the electrode 142 and the coil 158 at the point 64 can be used by the control circuitry 150 to generate the third "corner" of the PV loop 70. The pressure and volume are then measured during the isovolumetric relaxation phase (block 650). The point 52 may then be identified as the point on the PV loop at which the cardiac volume increases rapidly compared to an increase in the cardiac pressure. Pressure and volume measurements at the point 52 comprise the fourth "corner" of the PV loop 70 (block 660). Ventricular filling 50 from the point 52 to the point 56 can be approximated by a linear curve with a predetermined empirical slope which is well known in the art and which is easily found in the literature. In another embodiment, the point 52 can be established as the intersection of the path of isovolumetric relaxation 68 and the path of ventricular filling 50, as both of these paths are easily approximated.

Figure 7:
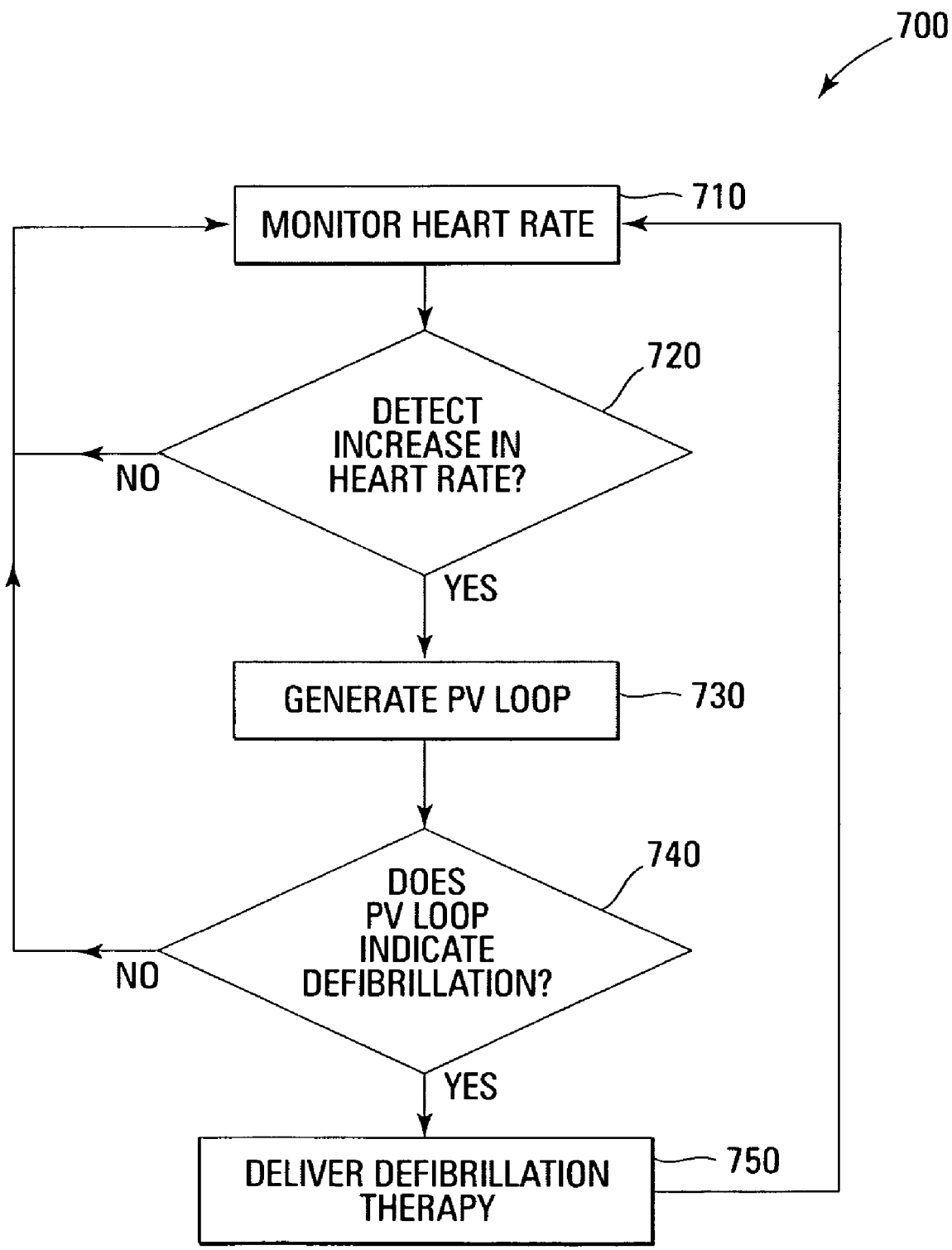
FIG. 7 illustrates an exemplary method of using an implantable medical device according to one embodiment of the present invention.

FIG. 7 shows an exemplary method 700 for detecting and treating ventricular fibrillation in the heart 8 using the IMD 110. First, the control circuitry 150 monitors the heart rate (block 710). Next, the microprocessor determines whether the heart rate has increased (block 720). Then, the control circuitry 150 generates a PV loop (block 730). In one embodiment, the control circuitry 150 generates a PV loop when the heart rate is between 120 to 165 beats per minute. Based on this PV loop, the control circuitry 150 determines whether the PV loop indicates defibrillation therapy is required (block 740). In one embodiment, this determination is made by comparing the generated PV loop to a baseline PV loop stored in the control circuitry 150. In one embodiment, the baseline PV loop is a PV loop for a normal human heart. In another embodiment, the baseline PV loop is a historical PV loop for the patient. In another embodiment, the generated PV loop may be compared to both a PV loop for a normal heart and a previously generated PV loop.

If therapy is indicated, the IMD 110 delivers defibrillation therapy (block 750) and then returns to monitoring the heart rate (block 710). If therapy is not indicated, the IMD returns to monitoring the heart rate (block 710). In an alternative embodiment, the control circuitry 150 notifies a clinician or stores the event in memory 155 for subsequent clinician care and/or display. In yet another alternative embodiment, the control circuitry 150 determines whether other therapy, such as pacing therapy or drug delivery, is warranted at any appropriate instance and delivers the therapy to the heart 8.

Figure 8:
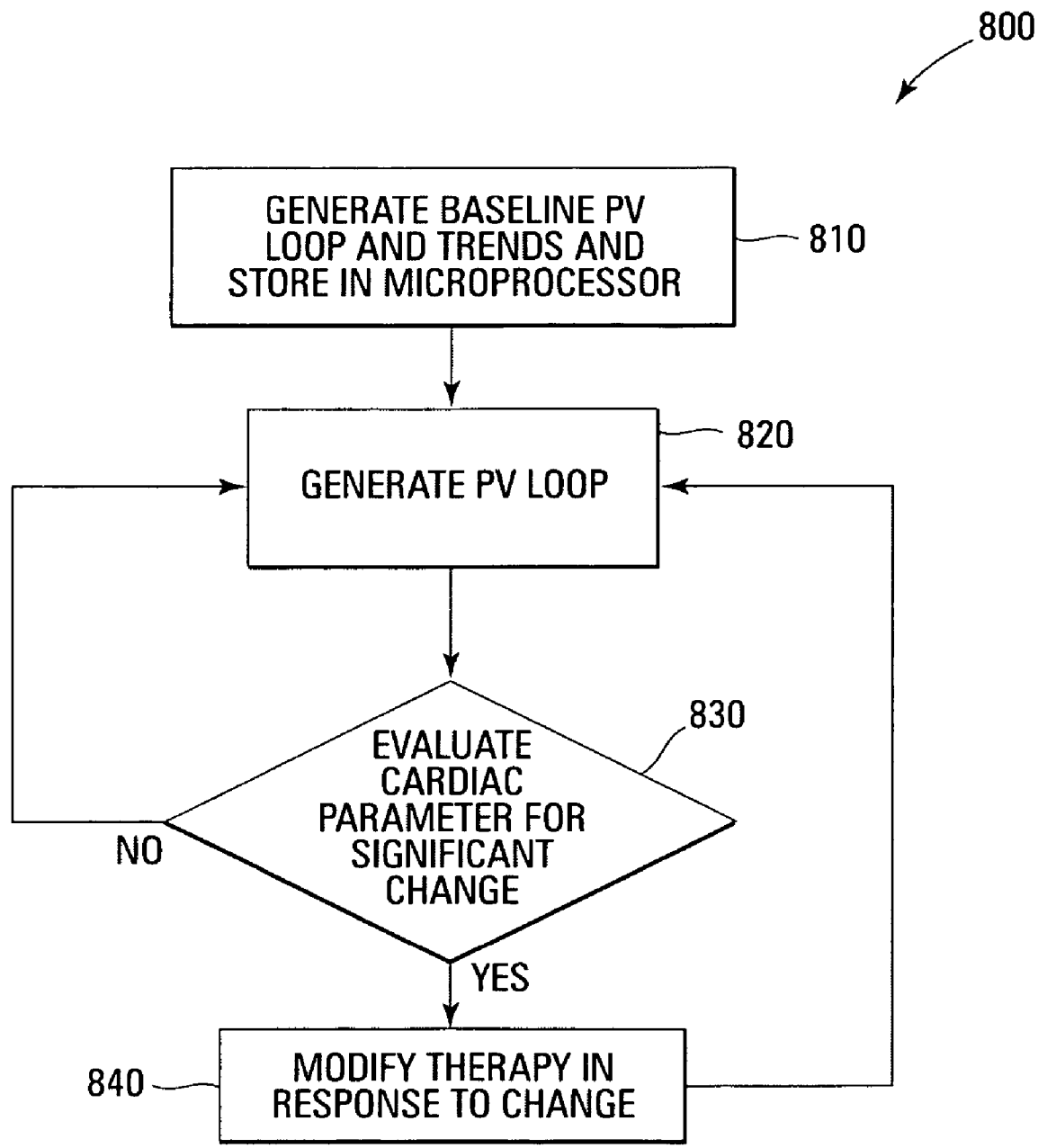
FIG. 8 illustrates another exemplary method of using an implantable medical device according to another embodiment of the present invention.

FIG. 8 shows an exemplary method 800 for modifying therapy to the heart 8 based on a generated PV loop. First, the control circuitry 150 generates and stores baseline cardiac PV loop and trends for cardiac pressure and volume parameters (block 810). In one embodiment, the stored trends include changes in the PV loop. Next, the control circuitry 150 generates a PV loop at a specified interval (block 820). The specified interval can vary in relation to the power available to the device and based upon the patient's condition. In one embodiment, the PV loop is generated daily. In another embodiment, the PV loop is generated hourly. In yet another embodiment, an increase in heart rate or cardiac pressure triggers the generation of the PV loop.

Next, the control circuitry 150 determines if a cardiac parameter has significantly changed (block 830), thus indicating therapy is required. In one embodiment, the cardiac parameter comprises the cardiac volume and the control circuitry 150 determines whether the cardiac volume has increased significantly. In another embodiment, the cardiac parameter comprises the contractility index and the control circuitry 150 determines whether the contractility index has decreased significantly. In yet another embodiment, the cardiac parameter comprises the ejection fraction and the control circuitry 150 determines whether the ejection fraction has decreased significantly. The evaluated cardiac parameter can include any other pressure or volume characteristic, or derivative of a pressure or volume characteristic that indicates performance of the heart 8. In one embodiment of the invention, the cardiac parameters are programmable values and the change sufficient to indicate therapy is required is left to the clinician's discretion. In another embodiment of the invention, the change sufficient to indicate therapy is required occurs when ejection fraction decreases below 50%.

If the evaluated cardiac parameter does not indicate that therapy is required, no further action is necessary and the control circuitry 150 returns to generating a PV loop at the specified interval (block 820). If the evaluated cardiac parameter does indicate that therapy is required, the control circuitry 150 and IMD 110 can modify the therapy as needed (block 840). In one embodiment, the therapy modification comprises delivering defibrillation therapy to the heart 8. In another embodiment, the therapy modification comprises releasing medication. In yet another embodiment modification comprises modifying pacing therapy delivered by the IMD 110. The control circuitry 150 then returns to generating PV loops to evaluate the result of the therapy modification (block 820). Alternative and additional steps include issuing a warning signal to the patient, transferring the data to an external database, and storing the data in memory 155 for evaluation by a clinician or display on an external device 159. In one embodiment, the PV loop is used to optimize lead placement during implantation of the IMD 110 using an iterative process of siting the lead, generating the PV loop, and re-siting the lead if necessary.

Various modifications and additions can be made to the exemplary embodiments discussed herein without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of generating a pressure-volume loop for a heart using an implantable medical device including a pulse generator having control circuitry, a first cardiac lead including a proximal end and a distal end, the cardiac lead coupled to the pulse generator at the proximal end, a first electrode located at the distal end of the cardiac lead and operatively coupled to the control circuitry, a sound sensor, and a pressure sensor, wherein the medical device is adapted to measure an intracardiac impedance using the first electrode, wherein the sounds sensor is coupled to the housing, and wherein the control circuitry is adapted to receive data from the sounds sensor, the pressure sensor and the first electrode and generate a pressure-volume loop using the sound, pressure and impedance data, the method comprising:

creating a first corner of the pressure-volume loop by recording a first cardiac pressure and a first cardiac volume at a first time associated with an S1 heart sound;

creating a second corner of the pressure-volume loop by recording a second cardiac pressure and a second cardiac volume at a second time at which cardiac volume starts decreasing;

creating a third corner of the pressure-volume loop by recording a third cardiac pressure and a third cardiac volume at a third time associated with an S2 heart sound; and creating a fourth corner of the pressure-volume loop by recording a fourth cardiac pressure and a fourth cardiac volume at a fourth time at which the cardiac volume increases rapidly.

2. The method of claim 1, wherein the cardiac volume is calculated based on an intracardiac impedance measured by the implantable medical device.

3. The method of claim 1, wherein the pressure-volume loop is used to measure a cardiac volume.

4. The method of claim 1, further comprising generating a baseline pressure-volume loop from pressure, volume and sound data, storing the baseline pressure-volume loop in the control circuitry, generating a second pressure-volume loop from pressure, volume and sound data at a specified interval, comparing the second press-volume loop to the baseline pressure-volume loop to determine if a cardiac parameter is changing, and if the cardiac parameter changes more than a predetermined amount, modifying a therapy delivered to the heart.

5. The method of claim 4, wherein the cardiac parameter is selected from the group consisting of a cardiac pressure, cardiac volume, an ejection fraction, a derivative of cardiac pressure, and a derivative of cardiac volume.

6. The method of claim 4, wherein the cardiac parameter comprises ejection fraction and, if the ejection fraction decreases below 50%, the therapy delivered to the heart is modified.

7. The method of claim 4, wherein the delivered therapy is selected from the group consisting of a pharmaceutical, a pacing therapy and a defibrillation shock.

8. The method of claim 1, further comprising detecting a heart rate and, if the heart rate is increasing, generating a first pressure-volume loop using pressure, volume and sound data, determining whether fibrillation is occurring based on the first pressure-volume loop and, if fibrillation is occurring, delivering a defibrillation therapy.

9. The method of claim 8, wherein the method further includes generating a baseline pressure-volume loop using the implantable medical device, storing the baseline pressure-volume loop in the control circuitry, and wherein the step of determining whether fibrillation is occurring includes comparing the first pressure-volume loop to the baseline pressure-volume loop.

10. The method of claim 8, wherein, if the heart rate increases to between 120 to 165 beats per minute, the first pressure-volume loop is generated.

* * * * *

UNITED STATES PATENT AND TRADEMARK OFFICE
CERTIFICATE OF CORRECTION

PATENT NO. : 7,580,746 B2 Page 1 of 1
APPLICATION NO. : 11/296732
DATED : August 25, 2009
INVENTOR(S) : Gilkerson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 734 days.

Signed and Sealed this

Fourteenth Day of September, 2010

David J. Kappos
*Director of the United States Patent and Trademark Office*